United States Patent
Montalbo

(10) Patent No.: US 7,130,693 B1
(45) Date of Patent: Oct. 31, 2006

(54) METHOD FOR INCREASING THE RESOLUTION AND DECREASING THE POWER DISSIPATION IN EYE PROSTHETICS

(75) Inventor: Joseph D. Montalbo, Menlo Park, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

(21) Appl. No.: 10/886,787

(22) Filed: Jul. 7, 2004

(51) Int. Cl.
*A61N 1/08* (2006.01)

(52) U.S. Cl. .................................................. 607/54
(58) Field of Classification Search .............. 607/54, 607/53; 623/6.63
See application file for complete search history.

(56) References Cited

U.S. PATENT DOCUMENTS

| | | | |
|---|---|---|---|
| 6,230,057 B1 * | 5/2001 | Chow et al. ........... | 607/54 |
| 6,324,429 B1 * | 11/2001 | Shire et al. ........... | 607/54 |
| 6,881,943 B1 | 4/2005 | Yegnashankaran | |

OTHER PUBLICATIONS

U.S. Appl. No. 10/218,836, filed Oct. 28, 2002, Mohan Yegnashankaran.

USC News Service. Oct. 1, 2003. "Center of Attention." 4pp.
US Santa Cruz Currents Online. Oct. 6, 2003. "New Engineering Center Focuses on Implantable Prosthetics." 3pp.
The National Science Foundation, Division of Engineering Education & Centers. "Program Areas." 5pp.

* cited by examiner

*Primary Examiner*—Scott M. Getzow
(74) *Attorney, Agent, or Firm*—Darby & Darby PC; M. David Ream

(57) ABSTRACT

A method for increasing a resolution and decreasing a power dissipation in an epiretinal implant device is described. The method includes positioning extendable microprobes to achieve mechanical contact with an anterior surface of the retina when the epiretinal implant device is activated. A level of pressure of the contact and an amount of current to be applied for stimulation of ganglion cells may be determined for optimum power consumption and stimulation. The contact of the microprobes with the retina, which may include MEMS, and an additional effect of mechanical stimulation enables reduction of current dissipation. Reduced current allows employment of more microprobes increasing resolution. The level of contact pressure and applied current may be dynamically re-determined based on changing ambient light conditions, and the like. A random duty-cycling of the mechanical contact and applied current may provide further reduction of current dissipation.

20 Claims, 6 Drawing Sheets

METHOD FOR INCREASING THE RESOLUTION AND DECREASING THE POWER DISSIPATION IN EYE PROSTHETICS

FIELD OF THE INVENTION

The present invention relates to eye prosthetics, and, in particular, to a method for improving retinal prosthetic implants through decreasing power dissipation and increasing resolution.

BACKGROUND

Various diseases result in destruction of rods and cones, essential elements of the retina converting light into signals to be transmitted to the brain. Loss of photoreceptor function contributes to blindness that may not be mitigated with conventional surgical methods. Retinal implants have been recently developed to replace damaged rods and cones and to provide electrical stimulation to ganglion cells. Ganglion cells translate electrical stimulation to electrochemical messages to be transmitted to specific regions of the thalamus and ultimately the visual cortex through the optic nerve.

Diverse techniques of translating optical information to electrical stimulation to the retina include capturing incoming light by a camera and transmitting it through a laser, wireless means, and the like to an implant device on the surface of the retina, within the layers of the retina, and the like. The device may then translate the optical information to an electrical signal and deliver it to the retina.

Because of constraints such as preserving intra-ocular temperature, power supply limitations, and the like, retinal implants may be limited in a resolution of the electrical signals they can provide to the retina.

Thus, it is with respect to these considerations and others that the present invention has been made.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Invention, which is to be read in association with the accompanying drawings, wherein.

DETAILED DESCRIPTION

Figure 1:
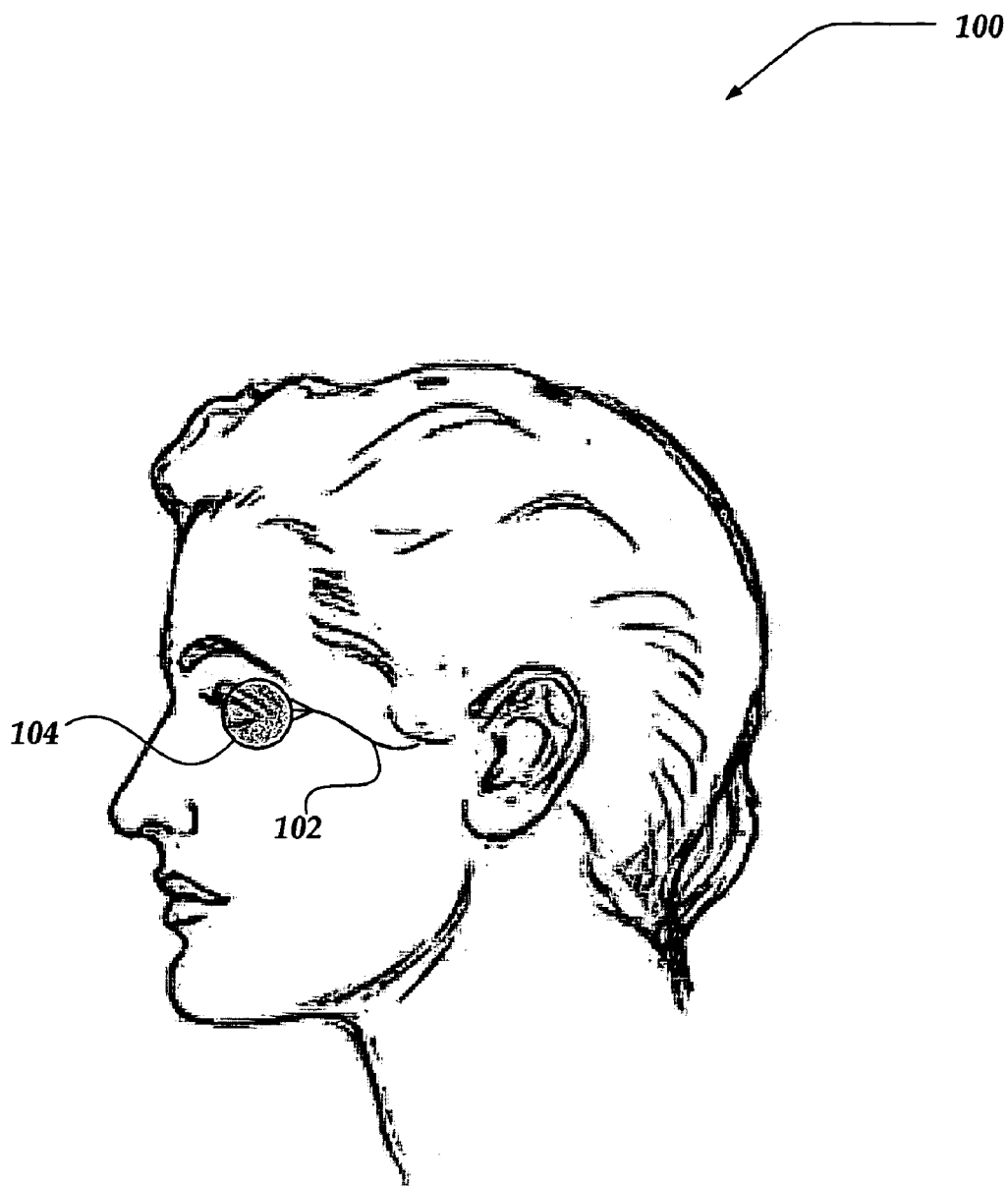
FIG. 1 illustrates a human head where the present invention may be implemented.

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or devices. Accordingly, the present invention may take the form of an entirely hardware embodiment or an embodiment combining software and hardware aspects. The following detailed description is, therefore, not to be taken in a limiting sense.

Briefly stated, the present invention relates to a method for improving retinal implant devices through decreasing power dissipation and increasing resolution.

Retinal implant devices may be used to restore visual perception to people suffering from damage to the retina due to diseases including retinitis pigmentosa, macular degeneration, and the like. These diseases may cause destruction of rods and cones in baciliary layer, but leave other cells of the retina largely intact. Application of electrical charges to the retina can elicit perception of light. By coupling optical sensing and communication mechanisms such as laser, wireless communication, and the like, it is feasible to develop biomedical smart implant devices that can support a significant number of stimulation points. Although development and use of artificial retinal implant devices is still in early stages, potential benefits of such technology are immense. Retinal implant devices may include epiretinal implant devices that are placed on an anterior surface of the retina, subretinal implant devices that are placed between layers of the retina, and the like.

Retinal implant devices may provide electrical signals to the retina. These electrical signals may be converted into electrochemical signals by ganglion cells and other underlying tissue structures and the response may be carried via optic nerve to the brain. Some of the challenges facing retinal implant devices are power supply, heat dissipation, adequate resolution, contact with retinal surface, external communication, and the like. An advantage of epi-retinal implant devices is the greater ability to dissipate heat because it is not embedded under the tissue. This is a significant consideration in the retina. The intra-ocular temperature is generally less than the normal body temperature of 98.6 degree Fahrenheit. In addition to a possibility that heat build-up from the epiretinal implant device could jeopardize a chronic implantation of the device, there is also a concern that elevated temperature produced by the epiretinal implant device could lead to infection, especially since the implant device could become a haven for bacteria. A risk of infection, long term damage, and the like, makes external supply of power to the epi-retinal implant device undesirable. This restriction coupled with the need to preserve the intra-ocular temperature makes is highly desirable for the epi-retinal implant device to have minimum power consumption. Furthermore, reduced power consumption may enable employment of a higher density of microprobes to stimulate the retina resulting in increased resolution.

At micro-levels, the anterior surface of the retina is highly irregular. Although some epi-retinal implant devices are made using flexible material, employment of fixed microprobes, such as microbumps, and the like, may lead to inconsistent delivery of a stimulation current to the retina. This, in return, may result in uneven resolution as well as higher than a desired current consumption.

The present invention employs a mechanical calibration for the microprobes and provides dynamic stimulation to the retina. The extendable microprobes may include Micro Electromechanical Systems (MEMS). First, the microprobes may be positioned based, in part, on an ambient light condition such that each probe touches the anterior surface of the retina with a same pressure. This will allow consistent contact with the retina and minimize an amount of stimulation current delivered to the retina. Additionally, by enabling each microprobe to touch the retinal surface, mechanical stimulation can be provided along with an electrical stimulation. The addition of the mechanical stimulation can reduce the amount of stimulation current, thereby the need for power for the epiretinal implant device. With the reduced current use a number of microprobes may be increased providing higher resolution. The positioning of the microprobes may be dynamically altered during operation, based on ambient light conditions, retinal surface changes, and the like.

Moreover, the stimulation current and a contact pressure applied by the microprobes may be duty-cycled dynamically such that cells may be engaged randomly. This approach may enable further reduction of a current consumption allowing use of more microprobes for increased resolution.

While a preferred embodiment of the present invention may be implemented in an epiretinal implant device, the invention is not so limited. For example, the described circuit may be employed in a subretinal implant device, a cortical implant device, a spinal implant device, and the like. Thus, the method may be implemented in virtually any epithelial implant device known to those skilled in the art.

FIG. 1 illustrates human head 100, where the present invention may be implemented. Human head 100 includes, in addition to usual features such as ears, mouth, nose, and the like, eyeball 104 and optic nerve 102.

Eyeball 104 resides in the ocular cavity and is connected to the brain through optic nerve 102. Optic nerve 102 receives an electrochemical signal from ganglion cells in eyeball 104 representing visual information and carries the signal to special regions of the thalamus and visual cortex in the brain. Optic nerve 102 also carries electrochemical signals from the brain to the eye.

Figure 2:
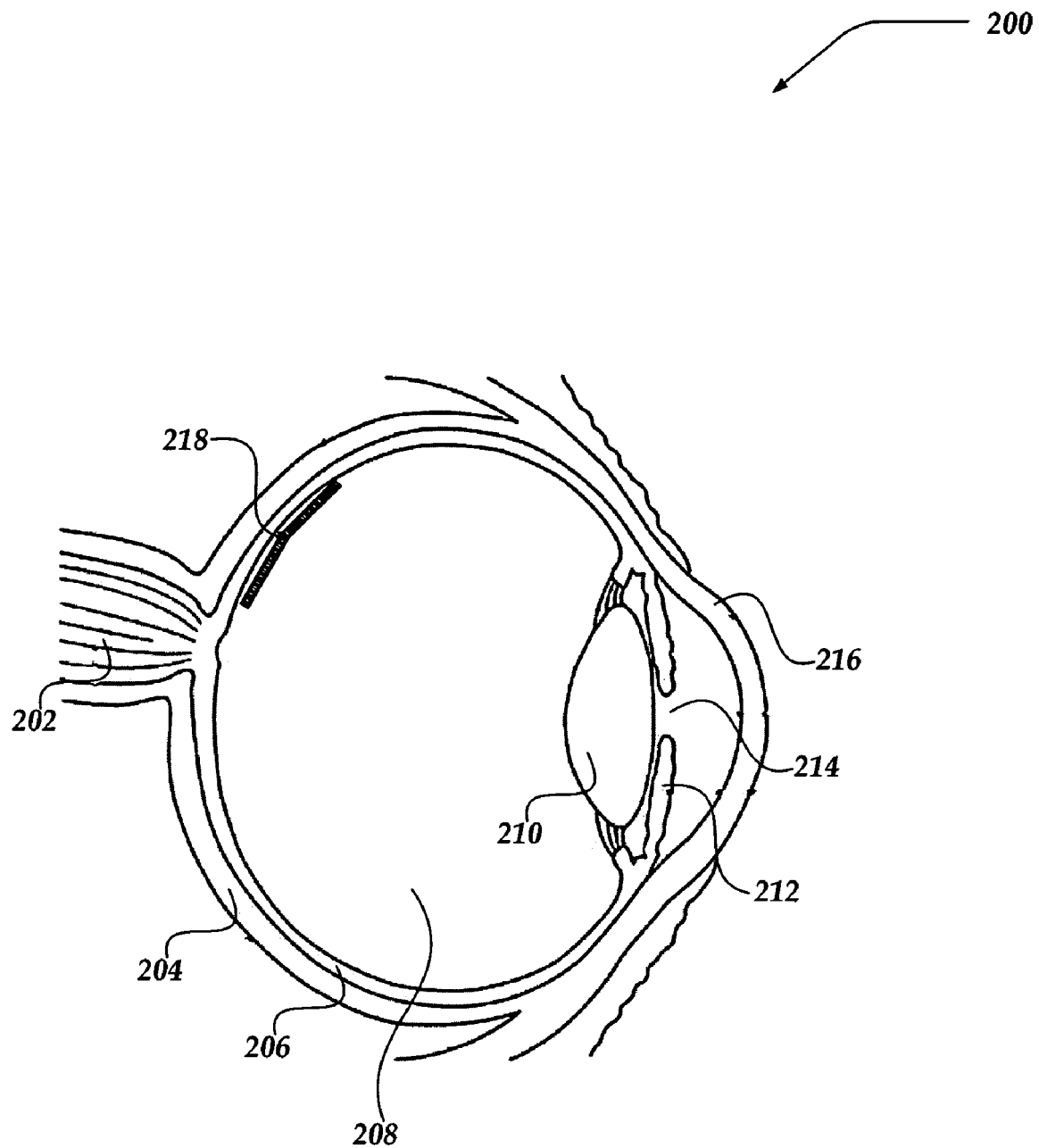
FIG. 2 illustrates an eye, with an epiretinal implant device.

FIG. 2 illustrates eye 200, with an epiretinal implant device. Eye 200 includes optic nerve 202, sclera 204, retina 206, vitreous humor 208, lens 210, iris 212, pupil 214, cornea 216, and epiretinal implant device 218.

Optic nerve 202 is a bundle of about a million nerves that carry electrochemical-signals corresponding to visual information from ganglion cells in retina 206 to the brain. Sclera 204 a white, non-transparent tissue, surrounds cornea 216 and provides protection to delicate inner structures of eye 200.

Retina 206 is disposed of an inner back wall of eye 200. Retina 206 includes several layers of specialized cells such as rods and cones, ganglion cells, optic nerve fibers, and the like. Rods and cones are photoreceptor cells in a bacillary layer that receive light arriving through iris 212 and lens 210, and generate electrochemical signals in response. A human eye may include 6–7 million cones. Research suggests the existence of three different types of cones one for red, one for blue and one for green color. Thus, the cones are primarily color sensitive photoreceptors. The rods are more numerous in human eye, about 120 million. While not color sensitive, the rods provide vision under dark, or scotoptic conditions. As mentioned above, diseases such as retinitis pigmentosa, macular degeneration, and the like may lead to destruction of a retina layer including the rods and cones degenerating vision significantly. In a healthy eye, the electrochemical signal generated by the rods and cones is captured by the ganglion cells in a different layer and transmitted to optic nerve fibers. Optic nerve fibers, distributed throughout retina 206, concentrate in one region and form optic nerve 202 connecting eye 200 to the brain.

Vitreous humor 208 is a gelatinous, clear liquid that fills the inner space of eye 200 surrounded by retina 206 and lens 210. Vitreous humor 208 enables preservation of a round shape of eye 200, and helps maintain an inner temperature of eye 200 slightly below a body temperature. Vitreous humor 208 is also critical in maintaining intra-ocular pressure.

Lens 210 is an internal focusing element of eye 200. Lens 210 controls about one third of a refraction of light that enters eye 200. Lens 210 is curved on both sides and attached to ciliary muscle at its top and bottom. A contraction and expansion of the ciliary muscle in response to a signal from the brain enables lens 210 to alter its shape and thereby a focus of eye 200. Lens 210 comprises soft material that allows the alteration of its shape, also called accommodation. In addition to controlling the focus of eye 200, lens 210 also controls the refraction of incoming light by absorbing particular wavelengths more than others.

Iris 212 is located on the outside of lens 210 and is made of very fine muscular tissue. Iris 212, which gives the eye its color, has a substantially round hole in its center. The hole is pupil 214. Pupil 214 controls an amount of light that enters eye 200 through lens 210. A size of pupil 214 is managed by contraction and expansion of the muscular tissue of iris 212. The size of pupil 214 changes based, in part, on an ambient light level. A response of pupil 214 is partially based on a stimulation of rods and cones of retina 206.

Cornea 216 is a clear tissue covering a front part of eye 200 including iris 212. Cornea 216 is a main source of refraction (about two third). Cornea 216 does not include any blood vessels, and is made of five clear layers of epithelium. Cornea 216's main task is to protect the eye against injuries and to provide a barrier against infection.

Epiretinal implant device 218 is a prosthetic device that may provide electrical, mechanical, electromechanical, and the like, stimulation to ganglion cells of retina 206 to compensate for damaged baciliary layer function. Epiretinal implant device 218 may include electrical circuitry for receiving optical information from an external source such as a CCD camera, and the like, determining characteristics of electrical signals to be generated in response to the received information and providing stimulation to the ganglion cells in form of electrical signals, mechanical stimulation, a combination of electrical and mechanical stimulation, and the like. A structure and function of epiretinal implant device 218 is described in more detail in conjunction with FIGS. 3 and 4 below.

Eye 200 includes many more components, and a structure and function of the listed components extend beyond the structures and functions described here.

Figure 3:
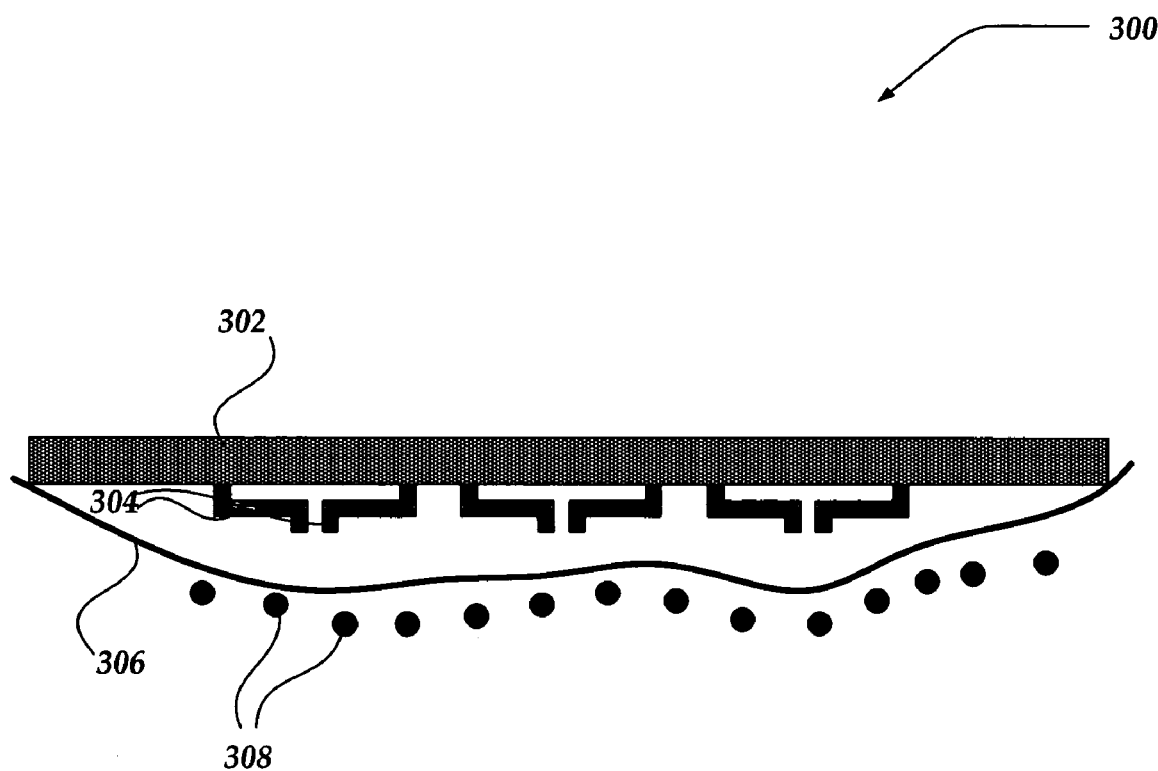
FIG. 3 illustrates an epiretinal implant device over an anterior surface of the retina with its microprobes in retracted position.

FIG. 3 illustrates diagram 300 showing an epiretinal implant device over an anterior surface of the retina with its microprobes in retracted position. Diagram 300 includes epiretinal implant device 302, microprobes 304, anterior surface of the retina 306, and ganglion cells 308.

Epiretinal implant device 302 includes circuitry for receiving and processing optical signals from an external source such as a CCD camera, and the like, and providing electrical signals to microprobes 304, which deliver the electrical stimulation to anterior surface of the retina 306. Epiretinal implant device 302 may include multiplexing circuitry, mechanical activation circuitry, and the like. In one embodiment, power may be provided to epiretinal implant device 302 through photosensitive cells on a top surface of the epiretinal implant device from a laser beam along with the optical signals. In another embodiment, power may be provided to epiretinal implant device 302 through RF induction.

Epiretinal implant device 302 may be manufactured employing a silicon based material and the like. Epiretinal implant device 302 may be flexible for a better fit to anterior surface of the retina 306. To reduce a risk of infection, damage over time, and the like, epiretinal implant device 302 may be coated with heparin, teflon, and the like.

Epiretinal implant device 302 may include on a bottom surface microprobes 304 for delivering electrical and mechanical stimulation to anterior surface of the retina 306. Microprobes 304 may include MEMS, and the like. Microprobes 304 may be manufactured employing durable material such as aluminum, titanium, platinum, platinum/iridium alloy, and the like. Because delivery of an electrical current in a saline environment is likely to cause corrosion over time, microprobes 304 may be coated with teflon, heparin, plastic, and the like. A construction of microprobes 304 may take into consideration a temperature, a pH level, a salinity of vitreous humor filling the space in the eye.

While FIG. 3 illustrates linearly lined up microprobes 304, in actual construction epiretinal implant device 302 may have a grid of microprobes 304. A number of microprobes 304 may depend on a current consumption of epiretinal implant device 302, a desired resolution, and the like. The number of microprobes 304 may determine a resolution of a visual stimulation. In an off-position, microprobes 304 may be aligned with the bottom surface of epiretinal implant device 302 not engaging anterior surface of the retina 306. When epiretinal implant device 302 is activated, microprobes 304 may be extended to engage anterior surface of the retina 306 providing mechanical stimulation as well as electrical stimulation through an applied current to ganglion cells 308 underneath the anterior surface of the retina.

Anterior surface of the retina 306 is a top layer of the retina. Ganglion cells 308 are located immediately underneath anterior surface of the retina 306. Ganglion cells 308 receive electrochemical stimulation from photosensitive cells (rods and cones) in a healthy eye and transmit the signals to the optic nerve.

Because a density and a distribution of photosensitive cells (rods and cones) varies throughout anterior surface of the retina 306, visual stimulation in a healthy eye is not uniform across the same surface. Therefore, different types of epiretinal implant devices 302 with varying microprobe densities may be implanted in different areas of anterior surface of the retina 306.

Figure 4:
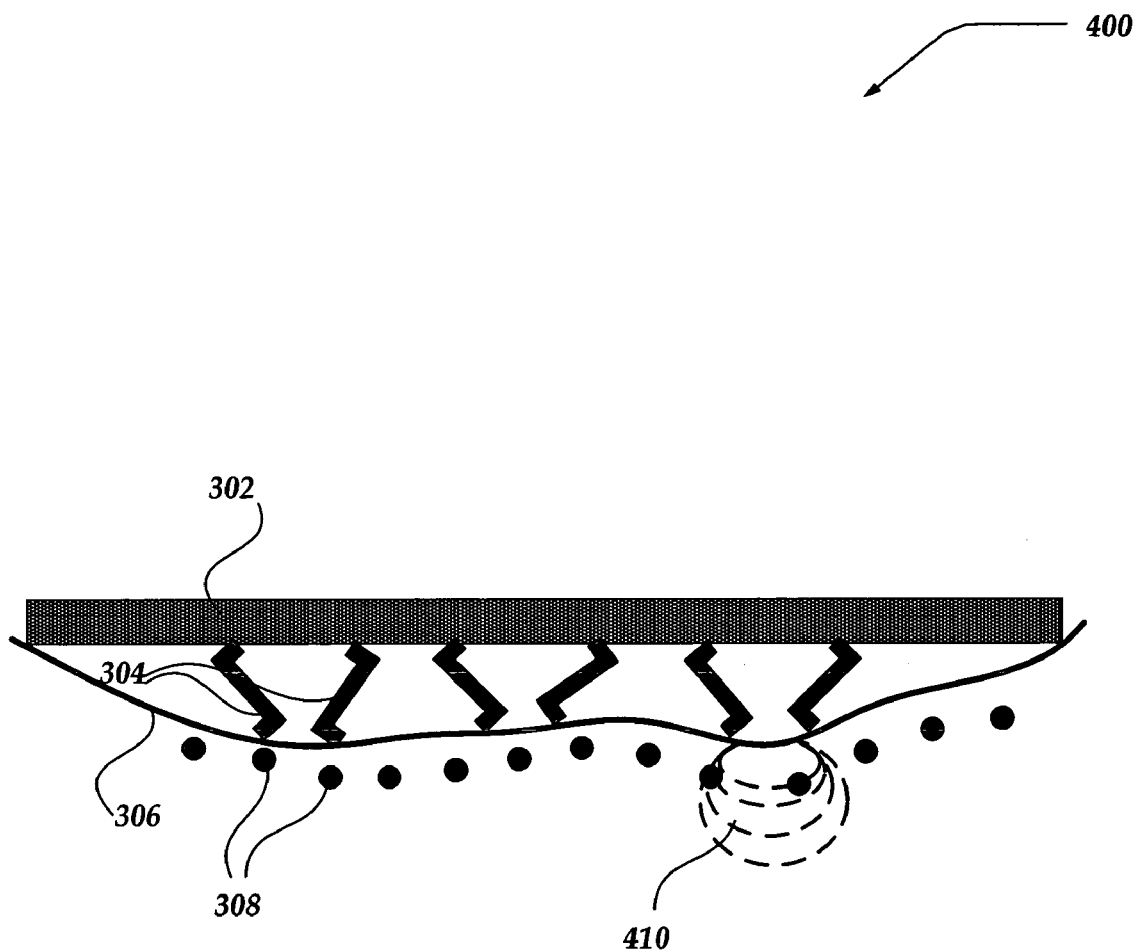
FIG. 4 illustrates an epiretinal implant device over the anterior surface of the retina with its microprobes in extended position.

FIG. 4 illustrates diagram 400 showing an epiretinal implant device over an anterior surface of the retina with its microprobes in extended position. Diagram 400 includes epiretinal implant device 302, microprobes 304, anterior surface of the retina 306, ganglion cells 308, and electrical current 410.

As described above, microprobes 304 may be aligned with the bottom surface of epiretinal implant device 302, not engaging the anterior surface of the retina, in an off-position. For optimum electrical stimulation a contact of each microprobe 304 with anterior surface of the retina 306 is desired. Furthermore, a mechanical contact of microprobes 304 with anterior surface of the retina 306 may provide additional stimulation. Thus, different levels of stimulation may be accomplished depending on whether microprobes 304 are in contact with anterior surface of the retina 306, a pressure of the contact by microprobes 304, and a level of current applied by microprobes 304.

When epiretinal implant device 302 is activated, a calibration process may be employed extending microprobes 304 such that contact with anterior surface of the retina 306 is achieved for each microprobe 304. In one embodiment, an ambient light level and available power for epiretinal implant device may be used to determine a pressure level for contact between microprobes 304 and anterior surface of the retina 306. Subsequently, the pressure applied by each microprobe may be modified to achieve optimum stimulation without causing damage to the retina. By adjusting the pressure applied by the microprobes, an amount of electrical current 410 applied for stimulating ganglion cells 308 may be reduced.

The calibration process may be repeated, if ambient light conditions change or a shape of the anterior surface of the retina changes due to variations in intra-ocular pressure, and the like. This dynamic adjustment of the position of microprobes 304 may enable reduction in current consumption by epiretinal implant device 302 allowing employment of more microprobes 302, thereby increasing the resolution.

In addition, a randomly patterned duty-cycle may be applied to the electrical and mechanical stimulation. For example, once optimum positions of microprobes 304 and the amount of electrical current 410 is determined, the microprobes may be randomly disengaged from the retina and reengaged. Similarly, electrical current 410 may be duty-cycled with a random pattern. The rods and cones of a healthy eye fire approximately once every 200–250 milliseconds. Thus, a random scanning pattern faster than once every 200 milliseconds may not be detected by the brain, while reducing a current consumption for epiretinal implant device 302.

Figure 5:
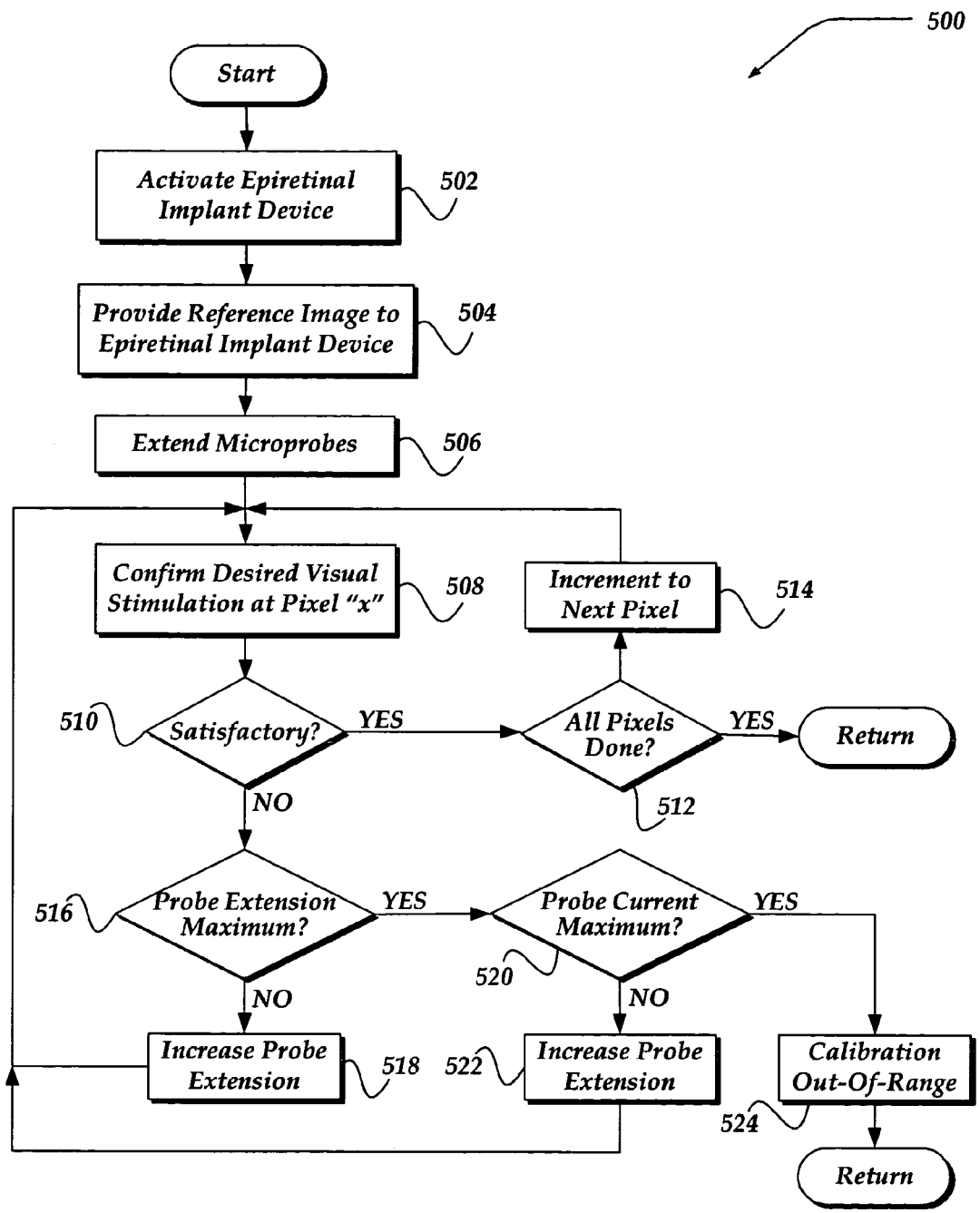
FIG. 5 illustrates a flow diagram generally showing a process of static calibration of an epiretinal implant device.

FIG. 5 illustrates flow diagram 500 generally showing a process of static calibration of an epiretinal implant device. As shown in the figure, process 500 begins after a start block, at block 502, where the epiretinal implant device is activated. Processing then proceeds to block 504.

At block 504 a reference image is provided to the epiretinal implant device for calibration. The calibration may be performed based, in part, on a level of ambient light, a desired resolution, and the like. Further, the calibration may be made by a preprogrammed computation process in the epiretinal implant device, provided by an external computer, and the like. Processing then proceeds to block 506.

At block 506, the microprobes are extended such that each microprobe pair contacts the anterior surface of the retina without damaging it and the current is applied to stimulate the ganglion cells. In one embodiment, the extension of the microprobes may be controlled to achieve that pressure level on the anterior surface of the retina. As described above, mechanical stimulation by the microprobes in addition to the electrical simulation may reduce a need for electrical current and increase resolution. An amount of current to be applied for stimulating ganglion cells may also be determined at block 506. Processing then proceeds to block 508.

At block 508, the desired visual stimulation may be confirmed for a selected pixel. The confirmation may be performed by measuring a signal level transmitted to the brain, receiving feedback from the person with the epiretinal implant device, and the like. Processing then proceeds to decision block 510.

At block 510, a decision is made as to whether the visual stimulation for the selected pixel is satisfactory or not. If the decision is affirmative, processing proceeds to decision block 521. If the decision is negative, processing proceeds to decision block 516.

At decision block 512, a decision is made whether the confirmation of visual stimulation has been completed for all pixels or not. If all pixels have been calibrated, processing returns to a calling process to perform further actions. If all pixels have not been calibrated yet, processing proceeds to block 514.

At block 514, calibration process is moved to a next pixel and processing returns to block 508 for calibration of the next pixel.

At block 516, a decision is made as to whether the microprobes are extended as far as they can be extended. If the decision is negative, the mechanical extension has not reached a maximum and processing proceeds to block 518, where the extension of the probes is increased and processing returns to block 508 for further calibration of the selected pixel. If the decision is affirmative, the microprobes have been extended as far as they can be and processing proceeds to decision block 520.

At block 520, a decision is made as to whether the current applied to the probes has reached a maximum level. If the decision is negative, the current has not reached its maximum level and processing proceeds to block 522, where the level of the current is increased and processing returns to block 508 for further calibration of the selected pixel. If the decision is affirmative, the current has reached its maximum, and processing proceeds to block 524.

At block 524, a determination is made that despite adjustment of the mechanical extension of the microprobes and the current applied to the microprobes to a maximum level, visual stimulation at the selected pixel was not satisfactory. This means, the pixel is out-of-calibration. Processing then returns to a calling process to perform further actions.

In one embodiment, changing ambient light conditions may be detected by an external photosensor and instructions sent to the epiretinal implant device for re-calibration. In another embodiment, an intra-ocular pressure may be monitored by the epiretinal implant device, by another device, and the like. Changes in the intra-ocular pressure may result in shape variation of the anterior surface of the retina. The epiretinal implant device may be programmed for re-calibration, if the intra-ocular pressure changes beyond a predetermined limit.

Figure 6:
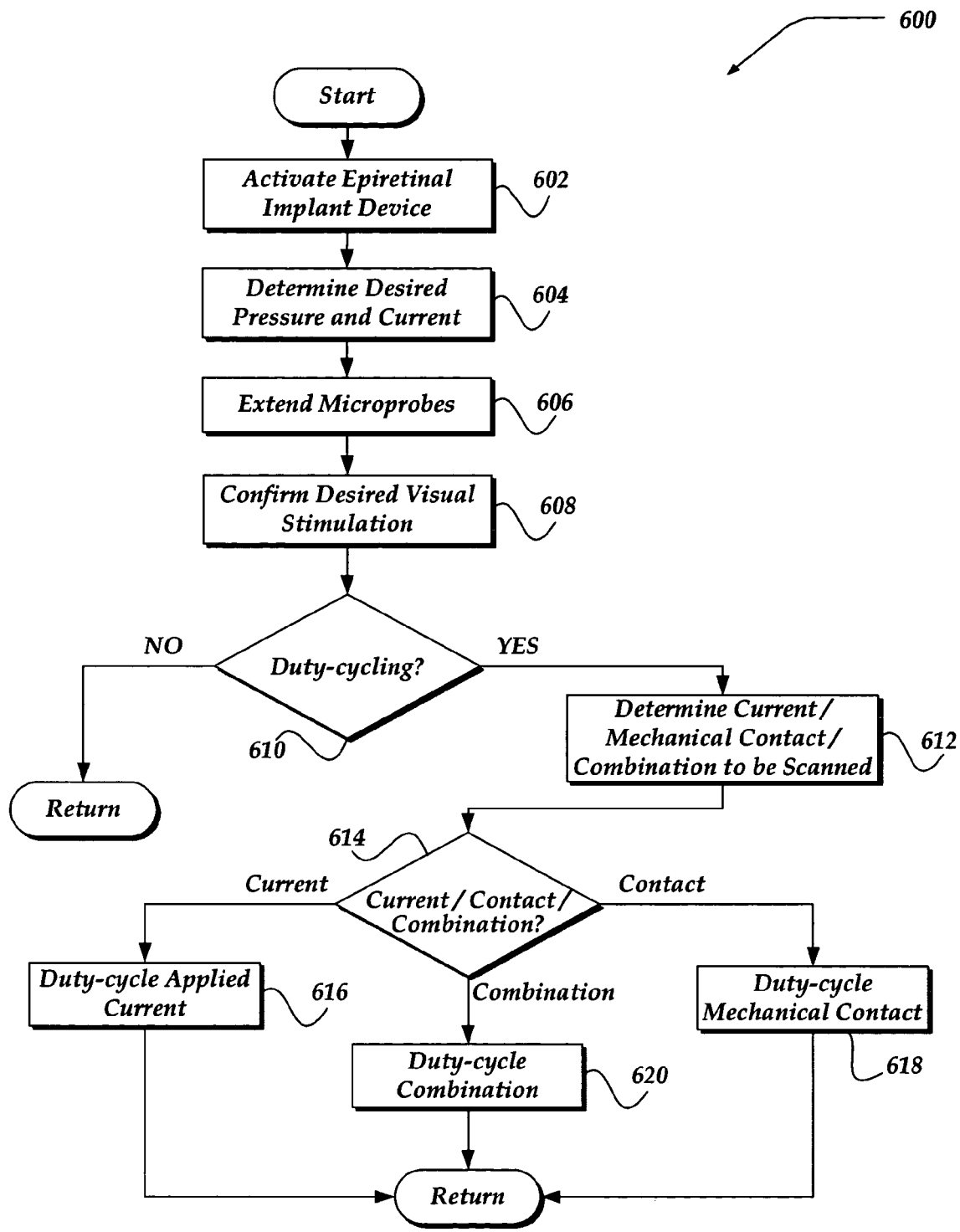
FIG. 6 illustrates a flow diagram generally showing a process of dynamically duty-cycled operation of an epiretinal implant device.

FIG. 6 illustrates flow diagram 600 generally showing a process of dynamically duty-cycled operation of an epiretinal implant device. As shown in the figure, process 600 begins after a start block, at block 602, where the epiretinal implant device is activated. Processing then proceeds to block 604. Blocks 604–608 are similar to blocks 504–508 of FIG. 5, where upon determination of a level of pressure and/or current, microprobes are extended, the current applied, and a desired visual stimulation confirmed. After block 608, processing proceeds to decision block 610.

At block 610, a decision is made, whether duty-cycling is to be applied. If the decision is negative, processing returns to a calling process to perform further actions and the epiretinal implant device operates without duty-cycling.

If the decision is affirmative, processing proceeds to block 612, where a type of duty-cycling is determined. As described before, photosensitive rods and cones, fire approximately once every 200–250 milliseconds. Thus, the brain may not detect a duty-cycle scan at a faster rate than once every 200 milliseconds. Duty-cycling of the applied current may enable a reduction of overall current consumption allowing employment of higher number of microprobes. This, in return, may result in an increase of the desired visual stimulation.

Mechanical contact by the microprobes provides additional stimulation as mentioned before. However, continuous mechanical stimulation may render exhaustive effects on the stimulated cells resulting in a reduction of overall performance. Accordingly, a duty-cycling of the mechanical contact may provide desirable resting to the ganglion cells and maintain the desired stimulative effect of the mechanical contact. In one embodiment, both the mechanical contact and the electrical current may be duty-cycled. Processing then proceeds to decision block 614.

At block 614, a decision is made whether duty-cycling will be applied to the current, the mechanical contact, or both. If the decision is duty-cycling the current only, processing proceeds to block 616. If the decision is duty-cycling the mechanical contact only, processing proceeds to block 618. If the decision is duty-cycling the current and the mechanical contact, processing proceeds to block 620.

At block 616, the applied electrical current is duty-cycled at a predetermined rate faster than once every 200 milliseconds. Processing then returns to a calling process to perform further actions.

At block 618, the microprobes are engaged and disengaged at a predetermined rate faster than once every 200 milliseconds. Processing then returns to a calling process to perform further actions.

At block 620, the applied electrical current and the mechanical contact are duty-cycled at a predetermined rate faster than once every 200 milliseconds. Processing then returns to a calling process to perform further actions.

It will be understood that each block of the flowchart illustrations discussed above, and combinations of blocks in the flowchart illustrations above, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor, provide steps for implementing the actions specified in the flowchart block or blocks.

Accordingly, blocks of the flowchart illustrations support combinations of means for performing the specified actions, combinations of steps for performing the specified actions and program instruction means for performing the specified actions. It will also be understood that each block of the flowchart illustrations, and combinations of blocks in the flowchart illustrations, can be implemented by special purpose hardware-based systems, which perform the specified actions or steps, or combinations of special purpose hardware and computer instructions.

The above specification, examples and data provide a description of the manufacture and use of the composition of the invention. Since many embodiments of the invention can be made without departing from the spirit and scope of the invention, the invention also resides in the claims hereinafter appended.

I claim:

1. A method for artificially stimulating a retina, comprising:
   receiving an optical input;
   determining an electrical current to be provided to the retina based, in part, on the optical input;
   independently extending each of a predetermined number of microprobes coupled to an epiretinal implant device such that each microprobe touches an anterior surface of the retina; and
   providing the electrical current to the anterior surface of the retina.

2. The method of claim 1, further comprising:
   determining a pressure to be applied by each of the microprobes to the anterior surface of the retina based, in part, on the optical input; and
   applying the determined pressure by modifying the extension of each microprobe.

3. The method of claim 2, further comprising:
   re-determining at least one of the electrical current or the pressure to be applied by the microprobes dynamically based, in part, on a condition; and
   modifying the extension of each microprobe based on at least one of the re-determined electrical current or the pressure to be applied by the microprobes.

4. The method of claim 3, wherein the condition is at least one of an ambient light level or an intra-ocular pressure.

5. The method of claim 1, wherein the microprobes are Micro Electromechanical Systems (MEMS).

6. The method of claim 2, wherein at least one of the electrical current or the applied pressure is duty-cycled at a predetermined rate.

7. The method of claim 6, wherein the predetermined rate is higher than about once every 200 milliseconds.

8. The method of claim 1, wherein the number of microprobes is pre-selected based, in part, on an area of the anterior surface of the retina where the epiretinal implant device is to be placed.

9. The method of claim 1, wherein a desired resolution is confirmed by:
   providing a predetermined optical input; and
   determining the desired resolution by employing at least one of user feedback or a measurement of a signal transmitted to the brain.

10. An epiretinal implant device, comprising:
    a body that is arranged to be placed on an anterior surface of a retina and to perform actions including:
       to receive an optical input;
       to independently extend each of a predetermined number of microprobes; and
       to provide a stimulation current to the microprobes; and
    the predetermined number of microprobes that are coupled to the body and arranged to perform actions including:
       to extend from the body such that a contact of each of the microprobes with the anterior surface of the retina is established; and
       to provide the stimulation current to the retina.

11. The epiretinal implant device of claim 10, wherein the body is further arranged to determine at least one of the stimulation current or a pressure to be applied by the microprobes based, in part, on a condition.

12. The epiretinal implant device of claim 11, wherein the condition comprises an intra-ocular pressure.

13. The epiretinal implant device of claim 10, wherein the microprobes are disengaged and re-engaged from the anterior surface of the retina based, in part, on a predetermined duty-cycle.

14. The epiretinal implant device of claim 10, wherein the stimulation current is duty-cycled based on a predetermined rate.

15. The epiretinal implant device of claim 10, wherein the microprobes comprise MEMS.

16. The epiretinal implant device of claim 10, wherein the microprobes are manufactured employing at least one of aluminum, titanium, platinum, or platinum/iridium alloy.

17. The epiretinal implant device of claim 10, wherein the microprobes are coated with at least one of teflon, heparin, or plastic.

18. The epiretinal implant device of claim 10, wherein the body is manufactured employing a flexible material including a silicon based material.

19. The epiretinal implant device of claim 10, wherein the epiretinal implant device receives power from an external source, through at least one of a laser beam or an RF induction.

20. An epiretinal implant device, comprising:
    a means for receiving an optical input;
    a means for determining a stimulation current;
    a means for determining a pressure to be applied to an anterior surface of the retina;
    a means for contacting the anterior surface of the retina, applying the determined pressure, and delivering the simulation current;
    a means for dynamically re-determining at least one of the stimulation current and the pressure to be applied; and
    a means for duty cycling at least one of the stimulation current and the pressure to be applied based, in part, on a predetermined rate.

* * * * *

UNITED STATES PATENT AND TRADEMARK OFFICE
CERTIFICATE OF CORRECTION

PATENT NO. : 7,130,693 B1
APPLICATION NO. : 10/886787
DATED : October 31, 2006
INVENTOR(S) : Joseph Domenick Montalbo It is certified that error appears in the above-identified patent and that said Letters Patent is hereby corrected as shown below:

Column 3; Line 52; Delete "electrochemical - signals" and insert -- electrochemical signals --, therefor.

Column 10; Line 44; In Claim 20, delete "slmulation" and insert -- stimulation --, therefor.

Column 10; Line 47; In Claim 20, delete delete "duty cycling" and insert -- duty-cycling --, therefor.

Signed and Sealed this

Seventeenth Day of April, 2007

JON W. DUDAS
*Director of the United States Patent and Trademark Office*